United States Patent [19]

Cioca et al.

[11] 4,295,894

[45] Oct. 20, 1981

[54] METHOD OF PREPARING SOLUBLE COLLAGEN FIBERS

[75] Inventors: Gheorge Cioca, Belleville; Marcel Siegler, North Bergen, both of N.J.

[73] Assignee: Seton Company, Newark, N.J.

[21] Appl. No.: 95,391

[22] Filed: Nov. 19, 1979

[51] Int. Cl.$^3$ .......................... C08L 89/06; C08K 3/24; C08K 3/20; C08K 3/30

[52] U.S. Cl. .................................. 106/155; 106/161; 260/123.7

[58] Field of Search ............... 106/124, 157, 161, 155; 260/123.7

[56] References Cited

U.S. PATENT DOCUMENTS

| | | | |
|---|---|---|---|
| 2,934,447 | 4/1960 | Highberger et al. ............... | 106/155 |
| 3,294,579 | 12/1966 | Tu ....................................... | 106/124 |
| 3,294,581 | 12/1966 | Hervey et al. ...................... | 106/124 |
| 3,408,918 | 11/1968 | Talty et al. ......................... | 106/155 |
| 3,634,561 | 1/1972 | Hawkins et al. .................... | 106/155 |

*Primary Examiner*—Allan Lieberman
*Attorney, Agent, or Firm*—Webb, Burden, Robinson & Webb

[57] ABSTRACT

A method of forming soluble collagen fibers from raw animal hides is disclosed. Raw animal hides are treated with an aqueous solution of an alkali metal hydroxide and a dehydrating agent to remove the hair and fat therefrom to yield a substantially fat-free corium. The interfibular bonds of the collagen in the corium are stabilized with an aqueous solution of an alkali sulfate. The corium is neutralized and dissolved in an aqueous acid solution to yield a collagen solution. The pH of the aqueous collagen solution is adjusted to the isoelectric point of the collagen to precipitate the collagen fibers from the solution. The collagen fibers are dried. The collagen fibers so produced are useful in edible food, may be redissolved and further processed for a plurality of uses.

16 Claims, No Drawings

METHOD OF PREPARING SOLUBLE COLLAGEN FIBERS

BACKGROUND OF THE INVENTION

This invention relates to collagen and more particularly to regenerated soluble collagen fiber.

"Natural insoluble collagen" as used herein means and refers to collagen which cannot be dissolved in an aqueous alkaline or in any inorganic salt solution without chemical modification and includes hides, splits and other mammalian or reptilian coverings. More particularly "natural insoluble collagen" means and refers to the corium which is the intermediate layer of a bovine hide between the grain and the flesh sides.

Collagen constitutes the connective tissue and is the major type of fibrous protein in higher vertebrae. Collagen in its natural state exists in a triple chain helix along with the constant periodicity between aligned triple chains. The triple chain helical configuration of collagen is sometimes referred to as a fibril and the fibrils align with an axial periodicity of about 640 A.

Although there are several types of collagen, the major type is referred to as "Type 1" which is the major collagen of skin, bones and tendons. The Type 1 collagen has a chain composition of $[\alpha 1(I)_2 \alpha 2]$. The $\alpha 1(I)$ and $\alpha 2$ chains are homologous.

In young animals there is little intramolecular and intrafibular crosslinking which provides for some degree of solubility of the collagen. However, during the aging process both intramolecular and intrafibular crosslinkings occur thus making the collagen insoluble.

Collagen and products derived therefrom have utility in the food, cosmetic and pharmaceutical fields. While it is known that collagen can be purified by the depolymerization of natural and soluble collagen along with subsequent reconstitution, the yields have been somewhat low and the resultant product is not always uniform.

U.S. Pat. No. 3,637,642 is exemplary of a process for dissolving insoluble collagen and regenerating the fiber.

Further, methods have been proposed for solubilizing and reconstituting collagen with the use of enzymes to sever intra- and interfibular bonds such as is disclosed in U.S. Pat. No. 3,034,852. Further, processes have been proposed for converting collagen fibrous masses to sheet-like material such as in U.S. Pat. Nos. 2,934,447 and 2,934,446.

Many processes of the prior art require that the treatment be conducted on the corium of the hide which is the collagen-rich source. To obtain the corium the hair is normally removed by liming or the like and the flesh containing a substantial amount of fat is normally stripped from the opposing side of the hide.

In accordance with the present invention a method of forming the soluble collagen fiber is provided wherein a raw hide is readily processed from its raw stage to form collagen fibers without complicated processes.

BRIEF DESCRIPTION OF THE INVENTION

Raw animal hides are treated with an aqueous solution of an alkali metal hydroxide and a dehydrating agent to remove the hair and fat therefrom to yield a substantially fat-free corium. The interfibular bonds of the collagen in the corium are stabilized with an aqueous solution of an alkali sulfate. The corium is neutralized and dissolved in an aqueous acid solution to yield a collagen solution. The pH of the aqueous collagen solution is adjusted to the isoelectric point of the collagen to precipitate the collagen fibers from the solution. The collagen fibers are dried. The collagen fibers so produced are useful in edible food, may be redissolved and further processed for a plurality of uses.

DETAILED DESCRIPTION OF THE INVENTION

"Raw hide" as used herein means and refers to an animal hide having the hair and flesh thereon.

In treating the raw hide with the aqueous solution of an alkali metal hydroxide and a dehydrating agent to remove the hair and fat therefrom the treatment should be conducted at room temperature. The alkali metal hydroxides useful in the practice of the invention are sodium hydroxide and potassium hydroxide. The dehydrating agent is preferably a low molecular weight highly polar organic solvent such as a lower alcohol or ketone such as methyl, ethyl or isopropyl alcohol or acetone, methyl ethyl ketone and the like.

The composition of the alkali metal hydroxide and the dehydrating agent aqueous solution should be about 40 percent to 50 percent of the dehydrating agent and 50 to 60 percent water, and 2.5 to 3 molar of the alkali metal hydroxide in the solution.

Typically, the raw hide is cut in pieces from 5 $cm^3$ to 10 $cm^3$ and treated at room temperature in the aqueous solution for at least 48 hours and up to 72 hours to remove the hair and fat from the hide to yield a substantially fat-free corium. The presence of the dehydrating agent reduces the swelling of the collagen fiber to allow the fiber to remain substantially intact while severing the teleopeptide bonds constituting the interfibular connection between individual collagen fibrils. The corium after the initial process of dehairing and defatting contains residual alkali metal hydroxide which must be removed.

Partial removal of the residual alkali metal hydroxide is accomplished by treating with a 20 to 60 percent aqueous solution of the dehydrating agent in order to remove these residual bass without substantial swelling of the collagen fiber. Most preferably, ethyl alcohol in aqueous solution is used for this purpose.

After treatment with the aqueous solution of the dehydrating agent, the corium is treated with the alkali sulfate for 0.5 to 5 hours, and preferably, 1 to 4 hours with strong stirring to remove any residual alkali metal hydroxide and further stabilize the intrafibular bonds of the collagen and to rehydrate the collagen. The collagen is then neutralized with an acid solution such as a 0.5 to 4 percent solution of boric acid, hydrochloric acid, tartaric acid, acetic acid, formic acid or the like. The pH of the neutralized collagen should be about 7.

Preferably, the neutralized collagen is placed in distilled water and agitated overnight to further remove residual salts.

The purified corium is dissolved in an aqueous solution containing 0.25 to 2 percent by weight of tartaric, citric, acetic or similar acid to yield a homogeneous collagen solution. The solution is homogenized and filtered to yield a homogeneous collagen solution at a concentration of about 0.5 to 3 percent by weight. This collagen solution is then precipitated by bringing the pH of the solution to the isoelectric point which is approximately 5.6 to 5.8. The isoelectric point is the point of zero potential where the pH value is neutral. Above or below this isoelectric point, the collagen acts either as an acid or as a base due to its amphoteric nature. Upon precipitation the dry reconstituted collagen fibers which are in discreet fibrous form are removed from the water by filtration or the like and dried by air drying, spray drying, freeze drying or the like.

The solution may be precipitated by the addition of a base such as dilute aqueous ammonium hydroxide, sodium hydroxide, potassium hydroxide or alkali earth metal hydroxides. When ammonium hydroxide is used its concentration should be at about 5 to 7 percent by weight as a precipitating agent. When alkali metal hydroxides or alkali earth metal hydroxides are used their concentration should be at about 1 to 2 percent by weight as precipitating agents. Salts such as sodium chloride may be used to precipitate the collagen fiber at the isoelectric point. When salts are used a greater than about 5 percent by weight solution is required, and 10 to 15 percent by weight solution is preferred as a precipitating agent.

Dehydrating agents may also be used as precipitating agents which do not bring the solution to the isoelectric point. These precipitating agents are acetone, ethanol, methanol or the like.

Additionally, a preservative such as potassium sorbate or the like may be added to the precipitating agent solution at levels of 0.01 to 0.5 percent by weight and more preferably 0.05 percent to 0.15 percent by weight.

The collagen fibers prepared in accordance with the invention can be stored for long periods of time thus providing a commercial collagen product.

The collagen fibers of the invention can be used as a texturizer for meat, as a food adjuvant, as a moisturizer for food, as an additive to cosmetic preparations and the like.

The invention will be further illustrated by the following example.

EXAMPLE 1

One kg of raw cow hide is charged to a suitably sized vessel.
A preformed solution having the following composition was charged to the vessel:
1600 ml of acetone
1400 ml of water
150 g of KOH
150 g of NaOH.
The hide was agitated in the solution for 48 hours to remove the hair and fat therefrom and provide a substantially pure corium. The treating solution was decanted and the vessel was charged with 3 liters of an aqueous ethyl alcohol solution. The corium was vigorously agitated in the aqueous alcohol solution for one hour. The alcohol solution was decanted and 3 liters of a 1 molar aqueous sodium sulfate solution was charged to the vessel. The corium was agitated for one hour in the sodium sulfate solution. The sodium sulfate solution was decanted and the corium was agitated with 3 liters of a 3 percent solution of boric acid for one hour to bring the pH value of the corium to 7.

The neutralized corium was placed in distilled water overnight to remove residual acid therefrom.

The purified corium was dissolved in 1 percent tartaric acid solution to provide a collagen solution of 1.5 percent; upon dissolution the solution was vacuum filtered.

One liter of the collagen solution was neutralized with 6 percent ammonium hydroxide to a pH of 5.7 (the isoelectric point), the collagen precipitated from the solution as discreet fibers. The water was decanted and the fibers were air dried.

The resulting dry collagen fibers can be stored for long periods of time, e.g. up to at least 3 months, without degradation.

Although the invention has been described with reference to specific materials and specific methods, it is only to be limited so far as is set forth in the accompanying claims.

We claim:

1. A method of forming soluble collagen fiber from a raw animal hide comprising:
    treating a raw hide with an aqueous solution of an alkali metal hydroxide and an organic dehydrating agent to remove the hair and fat therefrom, to yield a substantially hair and fat-free corium;
    stabilizing the interfibular bonds of the collagen in the corium with an aqueous solution of an alkali sulfate;
    neutralizing the corium;
    dissolving the corium in an aqueous acid solution to yield a collagen solution;
    precipitating collagen fibers from the solution; and
    drying the collagen fibers.

2. The method of claim 1 wherein said precipitation is accomplished by adjusting the pH of the aqueous collagen solution to the isoelectric point.

3. The method of claim 1 including treating the corium with a dehydrating agent prior to the stabilization of said interfibular bonds.

4. The method of claim 1 including washing the corium with distilled water to remove residual salts therefrom prior to dissolving the corium in aqueous acid solution.

5. The method of claim 1 wherein said dehydrating agent is selected from the group consisting of methyl alcohol, ethyl alcohol, propyl alcohol and acetone.

6. The method of claim 1 wherein the alkali metal hydroxide is sodium hydroxide, potassium hydroxide or mixtures thereof.

7. The method of claim 1 wherein said aqueous solution for treating the raw hide has 2.5 to 4 molar of alkali metal hydroxide, and 40 to 50 percent of dehydrating agent.

8. The method of claim 1 wherein said alkali sulfate is sodium sulfate.

9. The method of claim 1 wherein said alkali sulfate solution is 1 to 2.5 molar.

10. The method of claim 1 wherein the corium is neutralized with an aqueous acid solution.

11. The method of claim 10 wherein said aqueous acid solution is 1 to 4 percent of acid.

12. The method of claim 10 wherein said acid is boric acid or hydrochloric acid.

13. The method of claim 1 wherein said aqueous acid solution for dissolving said collagen is 0.5 to 2.5 percent acid.

14. The method of claim 13 wherein said acid is selected from the group consisting of tartaric acid, citric acid and acetic acid.

15. The method of claim 1 wherein said collagen solution is 0.5 to 3 percent by weight.

16. The method of claim 1 wherein the pH of said aqueous collagen solution is adjusted by aqueous ammonia.

* * * * *